United States Patent [19]

Carron et al.

[11] Patent Number: 5,402,709
[45] Date of Patent: Apr. 4, 1995

[54] METHOD AND APPARATUS FOR DETECTING STEAM IN A VOLUME OF AIR AND A STEAM GENERATOR AND A STEAM COOKING OVEN USING SUCH METHOD AND SUCH APPARATUS

[75] Inventors: Didier Carron, St. Maur; Philippe Deblay, Chatenay-Malabry; Robert R. DeSage, Verneuil/Sein, all of France

[73] Assignee: Cogia, Societe Anonyme, Orsay, France

[21] Appl. No.: 916,687

[22] Filed: Jul. 22, 1992

[30] Foreign Application Priority Data

Jul. 26, 1991 [FR] France ............................ 91 09527

[51] Int. Cl.6 ............................................ A21B 1/24
[52] U.S. Cl. .................................... 99/331; 99/473; 99/468; 126/369; 126/20; 219/401; 73/25.04; 73/295; 73/29.01; 374/45; 374/54
[58] Field of Search ............... 73/295, 29.01, 25.01, 73/25.04; 374/45, 54; 122/504, 13.2; 236/14, 44 E; 99/476, 473, 474, 342, 330, 331, 467, 468; 126/21 A, 369, 21 R, 20, 348; 219/401, 494, 497, 449

[56] References Cited

U.S. PATENT DOCUMENTS

| | | | |
|---|---|---|---|
| 4,682,013 | 7/1987 | Andre et al. | 219/497 |
| 4,717,811 | 1/1988 | Fujii | 219/497 |
| 4,911,357 | 3/1990 | Kitamura | 236/44 E |
| 5,014,679 | 5/1991 | Childs et al. | 99/476 |
| 5,038,752 | 8/1991 | Anson | 219/494 |
| 5,075,121 | 12/1991 | Desage et al. | 426/233 |

FOREIGN PATENT DOCUMENTS

| | | |
|---|---|---|
| 0188714 | 7/1986 | European Pat. Off. |
| 0335796 | 10/1989 | European Pat. Off. |
| 434798 | 10/1967 | Switzerland |
| 670515 | 6/1989 | Switzerland |
| 1335168 | 10/1973 | United Kingdom |
| 2207514 | 2/1989 | United Kingdom |

OTHER PUBLICATIONS

French Search Report and Annex.

*Primary Examiner*—David A. Scherbel
*Assistant Examiner*—Reginald L. Alexander
*Attorney, Agent, or Firm*—Sandler, Greenblum & Bernstein

[57] ABSTRACT

A method and apparatus are disclosed for detecting the presence of steam in a volume of air at a predetermined temperature. The apparatus includes a temperature sensor having two respective temperature build-up times representing an under steam temperature build-up time and an under air temperature build-up time. The method for detecting the presence of steam comprises the steps of placing the temperature sensor in the presence of the volume air, such that the sensor can reach a predetermined set point temperature that is lower than the predetermined temperature, taking a temperature measurement with the sensor, and determining if the measured temperature reaches the set point temperature in order to indicate whether the sensor is in the presence of steam.

17 Claims, 3 Drawing Sheets

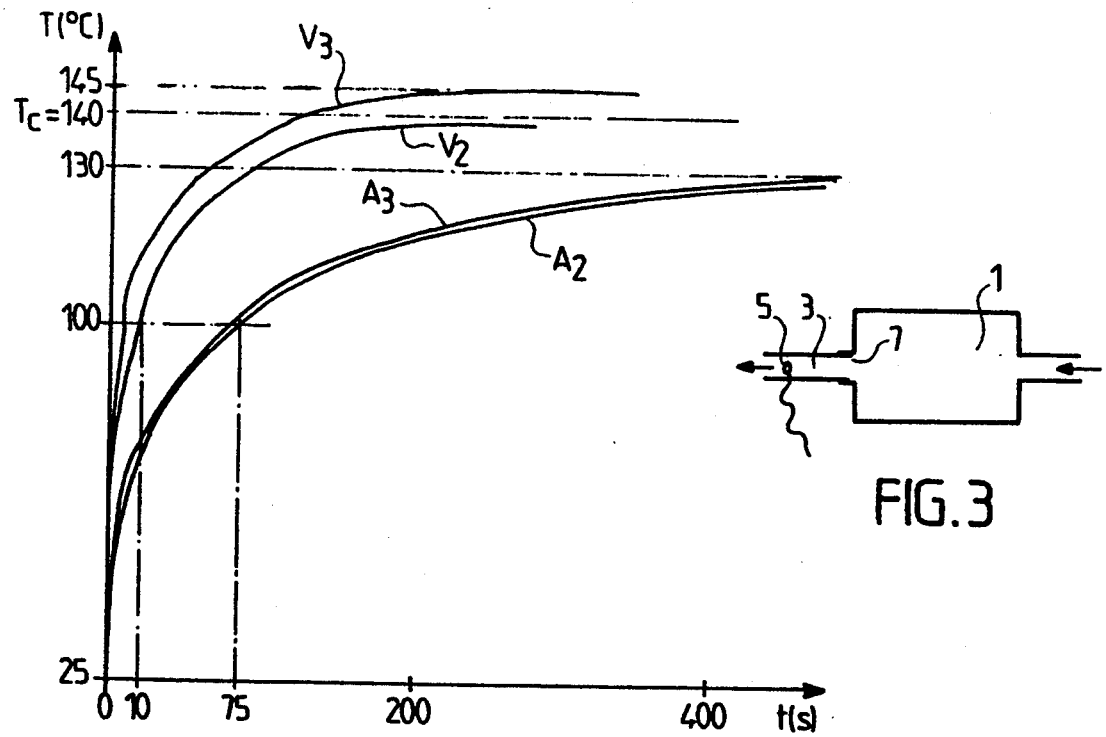
FIG. 2
FIG. 3
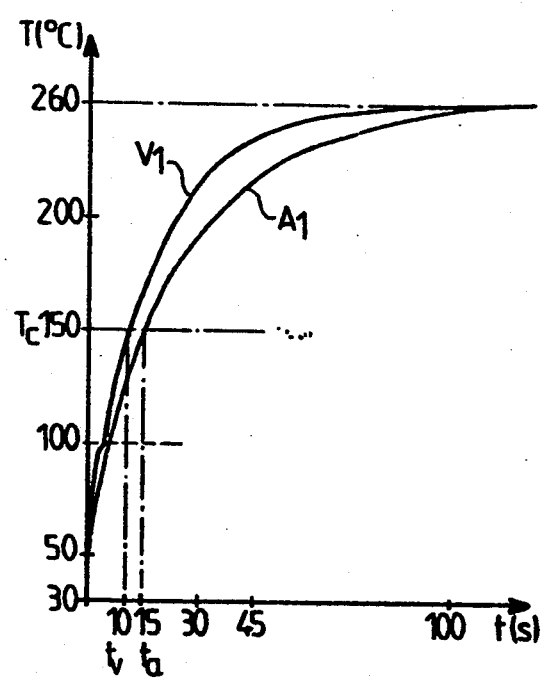
FIG. 1
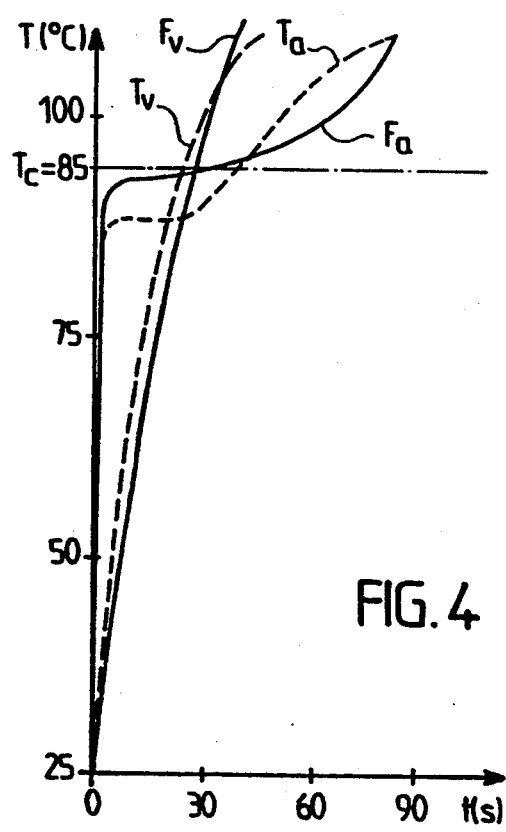
FIG. 4

METHOD AND APPARATUS FOR DETECTING STEAM IN A VOLUME OF AIR AND A STEAM GENERATOR AND A STEAM COOKING OVEN USING SUCH METHOD AND SUCH APPARATUS

BACKGROUND OF THE INVENTION

The present invention is related to a method and a device for detecting, in a volume of air at a given temperature, the presence of steam at the given temperature.

The present invention is also related to the application of this method and of this device, on the one hand, to the implementation of steam generators, preferably operating at atmospheric pressure, in order to provide them with a quasi-instantaneous response and, on the other hand, to checking the steam supplied by a steam generator to steam cooking ovens under atmospheric pressure.

The present invention is also related to a method and a device adapted to determine the percentage of steam, at a given temperature, that is possibly contained in an air mask at the given temperature.

Steam is used in numerous applications, both household as well as artistic and industrial, where it is necessary to obtain a specific detection of steam, (i.e., distinguishing steam at a given temperature from air at the same temperature). Such means can, for example, be used to supervise adequate and constant filling of steam in an enclosure, which may or may not have a thermostat, or yet again, for example, to detect the start of effective steam production of a steam generator, after a preheating period, or yet again, for example, to indicate any abrupt eruption of steam in a passage, for example, for safety reasons.

It is impossible to use a temperature sensor with a fixed post, to distinguish steam from air in a traditional manner because it is precisely the specific function of such sensors to indicate temperature, regardless of the nature of the gas.

It is possible, inversely, to this end, to use one of the numerous apparatuses or devices for measuring the degree of humidity of a gas, that are available commercially. These apparatuses and devices, mainly hygrometers and psychrometers use varied physical principles, namely expansion of air, changing the capacity of a hygroscopic polymer having a high dielectric constant, measurement of electrical resistivity, the temperature difference between a dry bulb and a moist bulb, cooling and analysis of dew point, etc. These techniques can provide the value of the percentage of humidity of a material with precision, and most of them, of a gas.

However, currently available devices, that provide more than just steam detection are relatively expensive and sophisticated because they provide a value close to the degree of humidity. Besides, the majority of hygrometers and psychrometers only function at relatively low temperatures, generally below 60° C., and only the most expensive apparatuses function correctly above 100° C. Certain devices, such as those implementing the technique of dry bulbs and moist bulbs, require that the apparatus be constantly re-supplied with a quantity of water that corresponds exactly to the evaporated quantity, and are thus delicate to implement.

When the above mentioned applications include establishing a steam flow, one could envision detecting such flow by means of gaseous flow measurement apparatuses, such as debitmeters. However, these measurement devices do not distinguish between air and steam, and do not therefore enable a specific detection of a steam flow, as opposed to an air flow.

We are therefore unaware of detection means specifically for steam, which are simple, strong, easy to implement and inexpensive.

SUMMARY OF THE INVENTION

The present invention thus aims at providing a method and a device for the specific detection of steam, possibly heated beyond the boiling point of water at atmospheric pressure, which is particularly simple to implement.

The object of the present invention is therefore a method for detecting, in a volume of air at a given temperature, the presence of steam, characterized in that it comprises the following steps consisting of:

placing, in the presence of the volume of air, at least one temperature sensor having two respective temperature build-up times, i.e., one temperature build-up time called "under steam" and one temperature build-up time called "under air", such that they enable it to attain a predetermined set point temperature, lower than the given temperature, when it is respectively in the presence of steam and in the presence of air, the sensor being placed in the presence of the volume either (1) in a zone capable of being subject to thermal loss such that when the volume of air is free of steam, the temperature sensor does not reach the set point temperature, and when the volume of air does contain a predetermined proportion of steam, or critical proportion, the temperature sensor reaches the set point temperature, or (2) during a time interval which is shorter than the "under air" build-up time and at least equal to the "under steam" build-up time;

undertaking a temperature measurement; and determining if the temperature measured reaches or does not reach the above-mentioned set point temperature, so as to indicate if the sensor is or is not in the presence of steam.

It is also the aim of the present invention to provide a device for detecting the presence of steam in a volume of air at a given temperature, characterized in that it comprises:

at least one temperature sensor having two respective temperature build-up times, namely one temperature build-up time called "under steam" and one temperature build-up time called "under air" such that they enable it to reach a predetermined set point temperature which is less than the given temperature, when it is respectively in the presence of steam and in the presence of air;

means adapted to create, in the vicinity of the temperature sensor, a zone subject to a thermal loss, such that when the air flow is free of steam, the temperature sensor does not reach the set point temperature and when the air flow does contain a predetermined proportion of steam, or critical proportion, the temperature sensor reaches the set point temperature, or means to place the temperature sensor in the presence of the volume for a time shorter than the "under air" build-up time and at least equal to the "under steam" build-up time;

means to undertake a temperature measurement;

means to determine if the measured temperature reaches or does not reach the above-mentioned set point temperature, so as to indicate if the sensor is or is not in the presence of steam.

As described hereinafter, the method and device for detecting steam according to the invention are based on tests conducted by the Applicant, enabling the Applicant to establish that the temperature build-up of the temperature sensors, placed in contact with a steam atmosphere at a given temperature, was much quicker than when the same sensors were placed in contact with an atmosphere constituted of air at the same temperature. Tests have shown that the time ratio taken to reach a predetermined set point temperature, respectively in a steam atmosphere and in an air atmosphere, could reach a value of 10.

The Applicant has also established that, although this ratio varies according to the type of temperature sensor used, the temperature build-up time of such sensor was, however, shorter most of the time (at equal air and steam temperatures), when it was in contact with steam, rather than when it was in contact with air.

In the method and in the device according to the invention, the temperature sensor can be of any type. One can thus use, among others, a bimetal, that has the advantage of being particularly inexpensive, but that has a relatively substantial inertia. One can also use more accurate sensors having less inertia, such as thermocouples, iron-nickel probes, platinum probes, varistors, resistors having positive or negative temperature coefficients, or any other temperature sensor.

Consequently, by analyzing the temperature build-up time of any sensor, (i.e., the time it requires to achieve a predetermined set point temperature) from a given temperature, it is possible to differentiate air from steam, at the same temperature, but also at clearly different temperatures, and especially, when the air temperature is greater than the steam temperature, as will be described hereinafter.

One can also use the same type of sensor in another way to obtain steam detection. It has thus been noted that when a temperature sensor is placed in an atmosphere crossed by a steam flow and/or an air flow that is subject to thermal losses, the temperature build-up times, respectively in the presence of steam and of air, are particularly contrasted because, as can be seen hereinafter, their ratios can climb to 20. This enables the difference in behavior of the sensor to be accentuated, depending on whether it is placed in the presence of a steam flow or an air flow, and thus enables the accuracy of detection to be heightened.

Additionally, it has been noted that when thermal losses are created, the thermal losses borne by air are greater, in relative value, than those borne by steam. Due to this fact, the air temperature falls more than that of steam. The temperature reached, at the end of an "infinite" period of time by the sensor, when air is free of steam, is therefore lower than the temperature reached when the air contains steam. Detection of steam can thus be undertaken, not only as mentioned hereinbefore, by examining the temperature build-up curves, but also by analyzing, at the end of any given time, the temperature reached by the sensor. By comparing this temperature with the values obtained during an earlier calibration, one can determine the presence or absence of steam in the gas. The sensor can be placed in any space which is subject to thermal losses, crossed by the gas flow (steam and/or air), the thermal losses thus created enabling air temperature to be lowered more quickly than steam temperature.

This space can, for example, be constituted of a tube, or any conduit of any shape, or even more simply, by ambient air itself. By varying the positioning of the sensor and the amounts of thermal loss, it is possible to implement the device according to the invention even if, for example, the air temperature is higher than the steam temperature. It is also possible to implement this device even when, after a first contact, the sensor remains in the presence of air or of steam. Indeed, in the latter case, it is possible to position the sensor in such a way that the equilibrium temperature of the sensor in air is lower than that of the sensor in steam, and thus exceeding the maximum temperature in air can be selected as the observation point and detection criterion of steam.

The present invention is also related to the applications of the method and of the device according to the invention. Its main aim is to disclose, on the one hand, a steam generator providing a quasi-instantaneous response, and on the other hand, a steam cooking oven provided with means for controlling the quantity of steam provided to the cooking enclosure of the oven.

Thus, an aim of the present invention is to provide a steam generator comprising an enclosure in which the water to be steamed is stored, steaming means adapted to bring the water contained in the enclosure to a boil, and to furnish, while exiting from such enclosure, a gas flow constituted of steam and/or air, characterized in that it comprises:

at least one temperature sensor located on the outlet path of the steam flow, the temperature sensor having two respective temperature build-up times, namely, one temperature build-up time called "under steam" and one temperature build-up time called "under air", such that they enable it to reach a predetermined set point temperature, lower than the given temperature, when it is respectively, in the presence of steam and in the presence of air;

means adapted to subject the gas flow exiting from the generator, in a zone located in the vicinity of the temperature sensor, to a thermal loss, this thermal loss being such that when the gas flow is free from steam, the temperature sensor does not reach the set point temperature and when the air flow does contains a predetermined proportion of steam, or critical proportion, the temperature sensor reaches the set point temperature; and control means of the steaming means, connected to the sensor, for stopping the operation of the steaming means when the sensor reaches the set point temperature.

When it is used on a steam generator, the device according to the present invention enables the generator to have a quasi-instantaneous response. The temperature sensor used has two temperature build-up times, to reach a predetermined set point temperature, when it is placed respectively in the presence of air and of steam at the same temperature. The temperature sensor is located in the vicinity of an outlet opening of the steam generator and controls the heating means of the generator, possibly by means of a control device, for example an all or nothing command or a proportionate command, in accordance with the temperature taken. In an all or nothing command, for example, the control device activates the heating means of the steam generator when the sensor is subject to a temperature that is less than a predetermined set point value, and deactivates such means when the temperature of the sensor reaches the set point temperature. This implementation enables one to obtain a generator with an instantaneous response, that is, immediately able to emit steam, at any moment, upon a simple request, and whose sensor only reacts to the steam. Indeed, the sensor oscillates between a temperature lower than the set point temperature when the generator does not produce steam (which activates steam production), and a temperature higher than the set point temperature when the generator produces steam (which results in stopping steam production). The generator thus always functions a little, and in fact compensates the thermal losses of the walls so that it maintains the liquid at its boiling point.

It is also the object of the present invention to provide a steam cooking oven comprising a cooking enclosure supplied with steam by a steam generator, the cooking enclosure being placed in communication with the ambient atmosphere by at least one outlet opening, characterized in that it comprises:

at least one temperature sensor, located on the outlet path of the gas coming out of the opening, so that it is in contact with such gas when it leaves the enclosure, the temperature sensor having two respective temperature build-up times, namely one temperature build-up time called "under steam" and one temperature build-up time called "under air" in order to reach a predetermined set point temperature lower than the given temperature, when it is respectively in the presence of steam and in the presence of air;

means adapted to subject the gas flow leaving the enclosure, in a zone located in the vicinity of the temperature sensor, to a thermal loss, this thermal loss being such that when the air flow is free from steam, the temperature sensor does not reach the set point temperature and when the air flow does contain predetermined proportion of steam, or critical proportion, the temperature sensor reaches said set point temperature, and control means for the steaming means, connected to the sensor, for stopping the operation of the steam generator when the sensor reaches the set point temperature.

According to the invention, the oven is constituted of a closed enclosure, communicating, on the one hand, with the outside by a reduced number of openings, and on the other hand, with a steam generator, within or outside of the enclosure. In the case of a steam generator outside the enclosure, communication with the steam generator is undertaken by means of a device for overheating the steam and capable of bringing such steam to a temperature clearly higher than 100° C., for example, about 200° to 300° C. Advantageously, the cooking enclosure is equipped with heating means, such as electrical resistors, inside or outside the enclosure, enabling such enclosure to be heated as well as the gas contained in it. These ovens comprise communication openings of the enclosure with the outside, and this enables one to ensure permanent natural pressure equilibrium between the enclosure and the outside of such enclosure, and the temperature sensor is positioned in the vicinity of one of these openings. The sensor controls the steam production obtained by the generator, possibly by means of a control device, for example, an all or nothing command or a proportionate command. In case of an all or nothing command, for example, the control device activates the generator when the temperature reached by the sensor is lower than a predefined set point temperature, and deactivates it when the temperature sensor reaches the set point temperature. This implementation basically enables the fulfillment of the following three functions.

Firstly, during start-up, it ensures control of air evacuation and steam-filling of the cooking enclosure. Indeed, various measures have shown that heat transfers from an air-steam mixture towards the food are proportionately greater and quicker when the proportion of air is smaller. The implementation of the method and of the device according to the invention enables one to ensure optimal evacuation of air initially contained in the enclosure in order to ensure a high proportion of steam therein. Indeed, when the generator starts to provide steam to the enclosure, the gas that exits from it is basically constituted of the air initially present in the enclosure, and is driven from it by the steam. Since the sensor build-up time, when it is in the presence of air, is relatively high, one ensures that the time required by the steam produced by the steam generator to drive out the totality of air present in the enclosure before beginning cooking, is less than the sensor build-up time under air. In these conditions, the evacuation of air thus continues until such a time that the gas leaving through the opening, in the vicinity of which the temperature sensor is located, is sufficiently rich in steam, so that the temperature sensor reaches the set point temperature. In this case, the sensor thus triggers the deactivation of the heating means of the steam generator. At this time, the cooking enclosure is only through-passed by a steam flow, and regulation is thereafter ensured, at the level of the sensor, by the exit of the steam.

Secondly, it ensures maintenance, during cooking, of satisfactory steam-filling of the enclosure. Indeed, at the start of the cooking, steam condenses on the food, and as such, there is consumption of steam in the enclosure. The result is a very brief return of air in the enclosure or, at least, a prolonged presence of air free of steam around the sensor. This air, passing especially through the sensor, makes the temperature read by the sensor to drop below the set point temperature, and this results in the activation of the heating means of the steam generator and, consequently, in steam production, such steam being provided to the enclosure until the steam requirement of such enclosure is satisfied, and until an excess flow exits through the opening in the vicinity of which the sensor is located. Inversely, at the end of cooking, when the food is hot, it begins to get dehydrated, and this results in steam being released so that an additional supply of steam is no longer necessary. The release of steam by the food results in a steam flow towards the outside which is detected by the sensor, which thus triggers the deactivation of the heating means of the steam generator.

Thirdly, it ensures that the enclosure is filled with steam after an opening and a closing sequence of the oven door. Indeed, as indicated previously, it is preferable that cooking be done in an atmosphere as close as possible to steam in order to maximize heat transfers. In the present example, the steam generator can, in an interesting manner, be disconnected during the opening of the cooking enclosure door, so that it does not send steam into the enclosure that would not be perceived by the sensor, because it would escape through the door. The generator is reconnected when the door is closed. As long as the steam introduced fills the enclosure and drives out air, the sensor is in contact with an air/steam mixture and reads a low temperature, so that it lets the generator provide steam to the cooking enclosure. Steam supply only stops when the cooking enclosure is full of steam, and an excess flow exits therefrom and sufficiently raises the temperature read by the sensor to reach the set point temperature.

It must be noted that an oven according to the invention procures two additional advantages, namely it minimizes steam yield, which enables, on the one hand, to reduce the amount of water consumed, and on the other hand, it reduces the amount of steam that escapes into the atmosphere, and finally it maintains, insofar as it is possible, a certain agitation of the gas within the cooking enclosure and this enables so as to benefit from the convectional movements of the steam therein, thus improving thermal exchanges.

In a variation of the embodiment of the oven according to the invention, it can additionally be equipped with an overheater, ensuring that the steam temperature provided by the steam generator can be raised beyond the boiling point of water at atmospheric pressure. This can be obtained, for example, in a very simple and known manner, by simply passing the steam exiting from the steam generator, along a heated resistor located in a tube. The steam can thus be easily heated to a temperature between 100° C. and 300° C., according to the power provided to the heating resistor.

The oven according to the invention can, naturally, be equipped with all normal heating means, compatible with the presence of steam in the enclosure, enabling food to be cooked and particularly, it can be equipped with electrical resistors. It can comprise control elements, such as a control device for the internal temperature of the cooking enclosure, popularly known as a thermostat, a timer or a programmer.

In another embodiment of the invention, a single temperature control device enables global adjustment of the temperature of the cooking enclosure and of the steam entering therein, the regulation being simultaneous though independent for each heating element.

The Applicant has also established that when the sensor is placed in the presence of a mixture of air and steam, it can be observed that it indicates a temperature build-up, whose rapidity is approximately intermediate with respect to the temperature existing in the presence of steam and the temperature existing in the presence of air, the temperature build-up being proportionately quicker when the proportion of steam in air is high. A calibration of temperature build-up times, recorded in this way, according to air/steam proportions, enables one to link a temperature build-up time parameter with this proportion. In predetermined usage conditions, one thus has a means for measuring the proportion of air/steam (i.e., means for measuring the hygroscopicity of the air).

It is also an object of the present invention to provide a method and a device for determining the proportion of steam possibly contained in a given mass of air.

The present invention thus aims to provide a method for determining a proportion of steam possibly contained in a mixture of air and steam at a given predetermined temperature, characterized in that it comprises the following steps consisting of:

determining, for at least one field of predetermined set point temperatures, the temperature build-up times "under steam" and "under air" of at least one temperature sensor, that is, the times necessary for it to reach a predetermined set point temperature, when it is successively placed in contact with steam and with air at the given temperature;

placing the temperature sensor in the presence of the volume of air until it reaches the set point temperature;

determining the temperature build-up time of the sensor in the mixture of air and steam; and determining the difference between the temperature build-up time measured by the sensor with the temperature build-up times "under steam" and "under air" of the sensor so as to deduce from it the proportion of steam contained in the volume of air.

It is also the object of the present invention to provide a device to determine the percentage of steam possibly contained in a mixture of air and steam at a given predetermined temperature, characterized in that it comprises:

a temperature sensor having two respective temperature build-up times, namely, one temperature build-up time "under steam" and one temperature build-up time "under air", so as to reach a predetermined set point temperature lower than the given temperature, when it is respectively in the presence of steam and in the presence of air;

means for placing the sensor in the presence of the volume of air for a time less than the "under air" build-up time and at least equal to the "under steam" build-up time;

means for undertaking, at the end of the contact time, a temperature measurement; and means for comparing the temperature build-up time measured by the sensor with the temperature build-up times "under steam" and "under air" of the sensor in order to deduce from it the proportion of steam contained in the volume of air.

BRIEF DESCRIPTION OF THE DRAWINGS

Hereinafter as an non-limiting example, an embodiment of the present invention, will be described with reference to the annexed drawings in which:

FIG. 1 is a graph representing the temperature reached by a heat sensor over the time during which it was respectively subjected to an atmosphere of steam at a given temperature, and to an atmosphere of air at the same temperature;

FIG. 2 is a graph representing the temperature reached by the heat sensor over the time during which it was respectively subjected to an atmosphere of steam at a given temperature, and to an atmosphere of air at the same temperature, the sensor being located in a zone subject to thermal losses and crossed by a gas flow constituted of air and/or steam respectively at 230° C. and at 320° C.;

FIG. 3 is a view representing, in a diagrammatic manner, the implementation methods used to obtain the graph of FIG. 2;

FIG. 4 is a graph representing the temperature reached by two different heat sensors, over the time during which they were respectively subject to an atmosphere of steam, at a given temperature, and to an atmosphere of air at the same temperature;

DETAILED DESCRIPTION OF THE INVENTION

Figure 5:
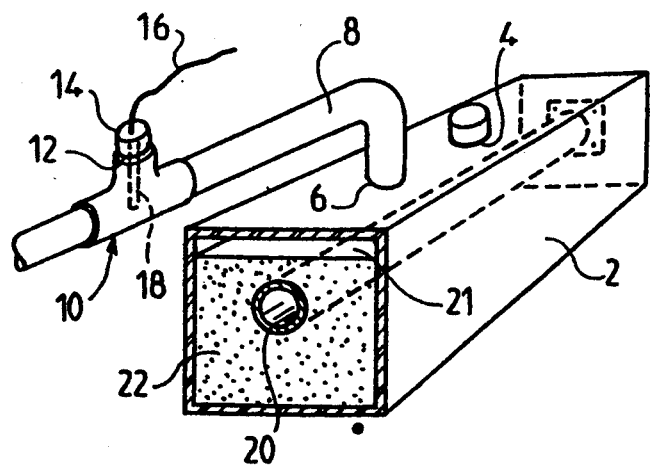
FIG. 5 is a perspective view, in a partial transverse section, of a steam generator according to the present invention.

The curves of FIGS. 1 and 2 illustrate the basic elements of the fundamental principle of the present invention. FIG. 1 represents the temperature reached by a heat sensor over the time that it was respectively in contact with a steam atmosphere and an air atmosphere at the same temperature. FIG. 2 represents the temperature reached by a heat sensor, over the time during which it was respectively in contact with a steam atmosphere and an air atmosphere, the sensor being located in a zone subject to thermal losses.

To obtain the curve of FIG. 1, the Applicant successively placed a temperature sensor 5, constituted of a thermocouple, in contact with a steam atmosphere at 240° C. and an air atmosphere at the same temperature. The temperature variations to which the temperature sensor 5 was subject has been represented over time. One thus notes that to reach a set point temperature Tc equal for example to 150° C., the temperature sensor, as represented on curve $A_1$, takes 15 seconds when it is in contact with air (the build-up time "under air" $t_a$ is thus 15 seconds) and only 10 seconds, as represented on curve $V_1$, when it is in contact with steam (the "under steam" build-up time $t_v$ being thus 10 seconds), in other words, a difference of 5 seconds. If one were to take, on the same curve of FIG. 1, a set point temperature $T_c$ equal to 80° C., one would note that the under steam build-up time $t_v$ is substantially half of the under air build-up time $t_a$. The difference in build-up times between $t_a$ and $t_v$ is advantageously used to detect the presence of steam in air either by "measuring" the build-up time of the sensor in order to reach a given set point temperature, or by "measuring" the temperature reached by sensor 5 at the end of a predetermined period of time.

As explained previously, the sensitivity of the method and of the device can be improved by locating sensor 5 in an environment crossed by an air and/or steam flow subject to thermal losses.

Thus, to obtain the curves of FIG. 2, as represented schematically in FIG. 3, steam and then hot air were successively injected at a given yield at 230° C., then at 320° C. into an enclosure 1 provided with an outlet opening 7, connected to an outlet tube 3 in which a heat sensor 5 was located, not far from the free end of tube 3, such that it was subject to thermal losses, and the temperature provided by sensor 5 was recorded over time. One thus obtains two curves $V_2$ and $V_3$, over time, corresponding respectively to a steam environment at 230° C. and at 320° C. and two curves $A_2$ and $A_3$ corresponding respectively to an environment of air at the same temperatures. An analysis of these curves shows that the differences in build-up times $t_a$ under air and $t_v$ under steam clearly increase.

Thus, for an air and steam temperature of 230° C. and a set point temperature $T_c$ of 100° C., the build-up time $t_a$ under air of sensor 5 is approximately 75 seconds whereas the build-up time $t_v$ under steam is only 10 seconds. This implementation method thus enables a particularly efficient improvement in the sensitivity and precision of steam detection. One notes additionally, that the curves obtained at temperatures of 230° C. and 320° C., respectively under air and under steam, are very close.

One also notes that the curves under air and under steam tend towards asymptotic values of the order, respectively, of 130° C. and of 145° C. This means, in physical terms, that for a given thermal loss, the sensor placed in an environment constituted exclusively of air cannot reach, under these operational conditions and regardless of the contact time, a temperature higher than 130° C., whereas the same sensor, when placed in an environment constituted exclusively of steam, can reach a temperature of 145° C.

In these conditions one notes that if one were to take a set point temperature $T_c$ comprised between the two asymptotic curves under steam and under air, namely, for example in the present case, a temperature of 140° C., the device according to the invention will be able to differentiate, at the end of any time period, air without steam from steam itself. Naturally, the set point temperature can be acted upon by modifying thermal loss, for example by bringing sensor 5 closer to or farther away from the free opening of tube 3.

As represented in FIG. 4, the Applicant has established, in substantially identical conditions, two pairs of curves of the same type (by using two different types of sensors), namely, a first pair of curves with an iron nickel sensor, respectively under air (curve $F_a$ and under steam ($F_v$) and the second pair of curves with a thermocouple also under air (curve $T_a$) and under steam (curve $T_v$), for an air and steam temperature of 135° C., close to a set point temperature $T_c$ of 85° C. As can be seen, curves $F_v$ and $T_v$ on the one hand, and $F_a$ and $T_a$ on the other hand are very close, which shows that steam detection according to the invention can be undertaken with sensors other than thermocouples, without substantial result variations.

The present invention is used, as represented in FIG. 5, to ensure the regulation of steam yield furnished by a steam generator.

The steam generator is constituted of a parallelopiped shaped enclosure 2, made of a plastic material such as, for example, polypropylene, and comprises, at its upper portion, an opening 4 blocked by a stop enabling enclosure 2 to be filled with liquid. Another opening 6 is also provided on the upper surface of enclosure 2, and is equipped with a flexible tube 8, for example made of silicon, that enables the steam produced by the generator to be evacuated. Tube 8 is interrupted, at a certain distance from enclosure 2, by a small T-shaped fixture 10, comprising a lateral opening 12. A stop 14 made of silicon is forced fitted in the lateral opening 12 of the T-shaped fixture 10 in order to ensure a perfect seal. This stop 14 is bored along its longitudinal axis with a very fine channel, through which a support wire 16 of temperature sensor 18 is introduced. This channel, compressed when stop 14 is pressed into T-shaped fixture 10, does not let gasses pass therethrough. The support wire 16 thus passes through stop 14 and temperature sensor 18 is located in such a way so as to be at the center of tube 8, without touching the walls of the latter.

The temperature sensor 18 used is a thermocouple of the type whose temperature variation curve over time under steam and under an air atmosphere is represented in FIG. 2. This thermocouple 18 has two respective build-up times in order to reach a set point temperature $T_c$ of 100° C. when it is respectively in the presence of steam at 320° C. and air at the same temperature, namely a first build-up time (under steam) $t_v$ equal to approximately 10 seconds and a second build-up time (under air) $t_a$ equal to approximately 75 seconds.

Enclosure 2 comprises, additionally, an electrical resistor 20, for example of the cartridge type, that is, constituted of a tubular element made of stainless steel inside which the actual electrical resistor is housed, having a power of approximately 1200 watts, such tubular element being fixed, at its ends, to two lateral walls of enclosure 2, by fixing means not represented in the drawing.

A porous body 22, constituted for example of rock fibers, and preferably comprising a bond adapted to especially promote its mechanical retention, is located in a compressed state, in enclosure 2 around resistor 20 so as to ensure good mechanical contact therewith, and thereby, a good heat transfer. A space 21 is left free between the upper surface of porous body 22 and the upper internal surface of enclosure 2 so as to allow expansion of the steam produced.

Figure 6:
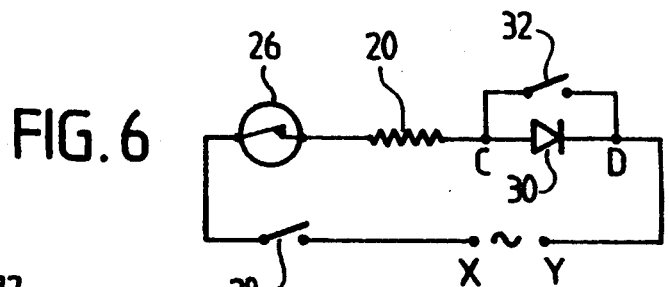
FIG. 6 is a diagrammatic view of an electrical supply circuit of the steam generator of FIG. 5.

The present device is supplied with electrical power by means of an electrical control circuit represented in FIG. 6. At points X and Y of the electrical network are successively connected, serially, a general interrupter 28, a contact 26 linked to temperature sensor 18, which enables current to pass through as long as the threshold temperature is not reached, a resistor 20 and a diode 30 being connected at points C and D from which an interrupter 32 is mounted in parallel, this interrupter 32 allowing, when it is open, only to let half the nominal power of the generator to pass through, such that, for example, the oscillation phases of sensor 18 are slowed down.

In these conditions, the functioning of the steam generator is as described hereinafter. Before the activation, the user introduces the liquid to be steamed in enclosure 2 via opening 4, after removing the closure stop, until the level of the liquid skims the base of porous body 22. During the activation of the device, that is as soon as the general interrupter 28 is closed, resistor 20 of the steam generator starts to heat the liquid contained by impregnation in porous body 22. At the end of a given period of time, the water contained in porous body 22 surrounding resistor 20 reaches its boiling point, and starts to produce steam. The steam produced first pushes out the air initially present in enclosure 2, which leaves via tube 8.

The steam yield of the steam generator will be such that the total evacuation of air contained in space 21 of enclosure 2 is obtained in a time less than the under air build-up time $t_a$ of sensor 18 (i.e., in the present case, less than 75 seconds), in order to stop sensor 18 from reaching the set point temperature $T_c$ before all the air from enclosure 2 has been evacuated, which could result in a premature stop of steam production.

This air evacuation phase continues as long as most of the air is not driven out by the steam, and as long as a substantial quantity of steam is not present in the evacuated air. Once the exiting air steam flow is basically constituted of steam, there is a quick rise in the temperature of sensor 18, and when this temperature exceeds the set point temperature $T_c$ of 100° C., after a time period necessarily greater than $t_v$ (i.e., in the present case 10 seconds), contact 26 of thermocouple 18 opens, thereby cutting off resistor 20 of the generator. The enclosure is then filled with steam. The steam production is interrupted and the generator passes to the resting state. As soon as the steam flow is suppressed in tube 8, the temperature of temperature sensor 18 starts to fall below set point temperature $T_c$ of 100° C., and contact 26 of the sensor is closed, retriggering steam production. A maintenance cycle can thus be established, ensuring periodic steam production that maintains a constant filling of steam in enclosure 2.

Naturally, the method and the device for detecting steam according to the invention can be used with steam generators provided with any heating means, and especially electrodes, between which a compressed porous body is located, containing the liquid to be steamed and that is electrically powered.

The method and device for detecting steam are particularly interesting in order to ensure, in a simple, precise and economical manner, the regulation of steam flow supplying an oven adapted to cook food.

Figure 7:
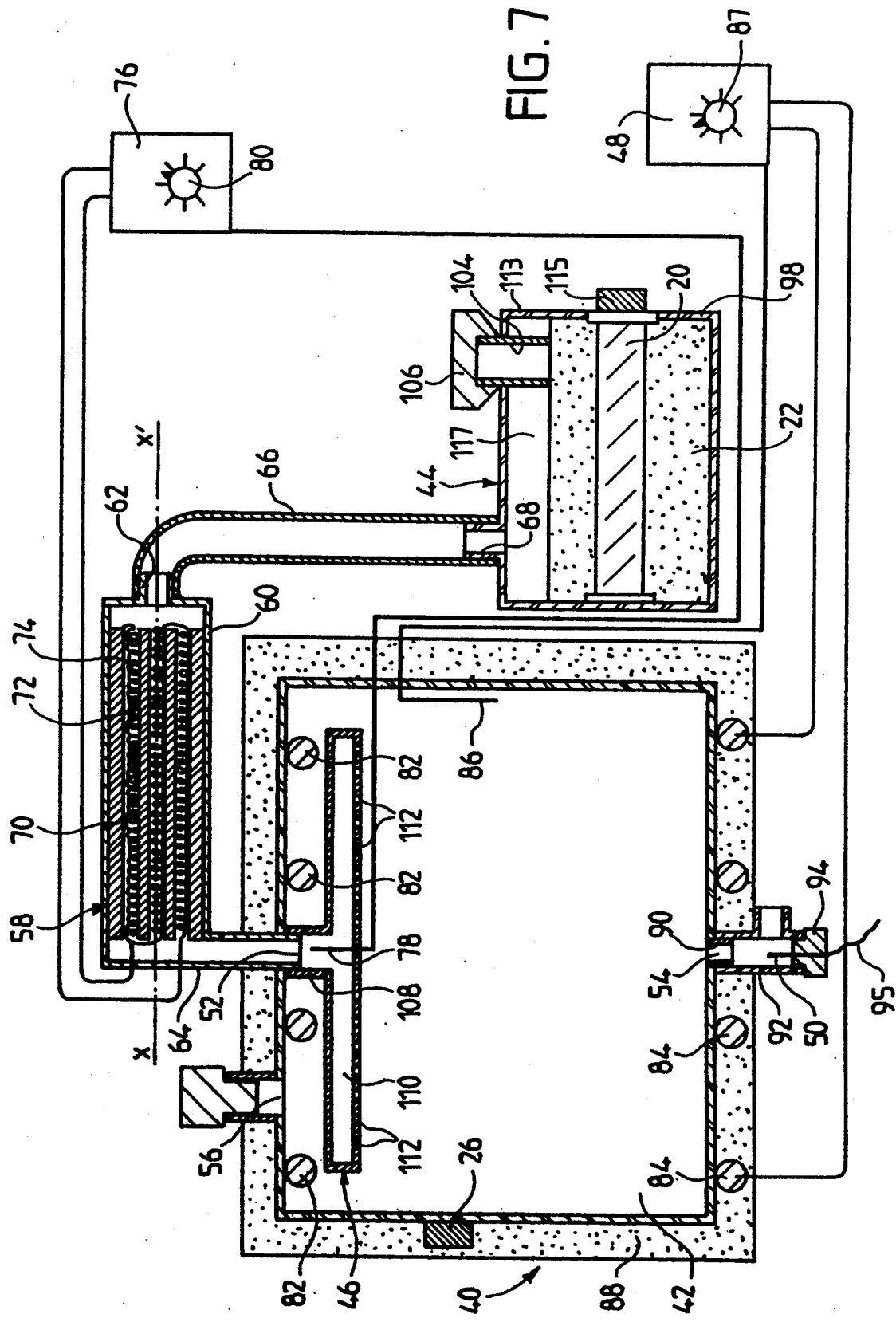
FIG. 7 is a transverse sectional view of a cooking oven according to the present invention.

Thus, in FIG. 7, an oven 40 is mainly constituted of a cooking enclosure 42, of a steam generator 44, located outside enclosure 42, a device 46 for distributing steam into enclosure 42, means for regulating 48 the temperature of enclosure 42, which can be adjusted by means of a control 87, a device for detecting steam, basically comprising a temperature sensor 50, and a device for electrical supply. The cooking enclosure 42, shaped like a parallelopiped, is composed of five metallic planar surfaces, constituting the roof, the floor, the sides and rear, and of a frame equipped with a door, not represented in the drawing.

The cooking enclosure 42 has three openings, namely, one steam inlet opening 52, one outlet opening for the air/steam mixture 54, and one safety opening 56 enabling quick evacuation of gas in case of accidental over pressure.

Although an overheater is not obligatory to the implementation of the present invention, the steam inlet opening 52 is, in the present embodiment, connected to a steam generator 44 by means of an overheater 58. The latter element, adapted to raise the temperature of steam entering the cooking enclosure 42 beyond 100° C., is basically composed of a stainless steel tube 60, having a longitudinal axis xx' that opens at its opposite ends, on two tubes having a smaller diameter, namely, an inlet tube 62 and an outlet tube 64. The inlet tube 62 is joined to a flexible pipe 66 connected to an outlet tube 68 of steam generator 44, so as to enable entry of steam into overheater 58. The outlet tube 64 is linked to the steam inlet opening 52 of cooking enclosure 42. A cylindrical chuck 70, made of refractory ceramic, bored in the direction of length xx' of a series of cylindrical channels 72 is located inside tube 60. A wire, for example made of material commercialized under the trademark "KANTHAL", having a resistivity of approximately 25 Ohms per meter, and wound about itself to form a helical spring, is located in each of its seven channels 72 so as to form an electrical resistor 74. The ends of such cylindrical resistor 74 are electrically connected to regulatory means 76 ensuring the start and stop of overheater 58, and are adjustable by control means 80.

A first temperature sensor, constituted of a thermocouple 78, is located in the vicinity of steam inlet opening 52 of cooking enclosure 42. This sensor 78 measures the temperature of the steam exiting from overheater 58 and admitted into enclosure 42. This thermocouple 78 is electrically connected to regulatory means 76, so as to control the functioning of overheater 58, as per a temperature selected and displayed by means of a control 80.

The cooking oven according to the invention is equipped with two heating resistors shaped like a double U, namely a first resistor 82, suspended beneath the ceiling of enclosure 42, both of whose ends comprise electrical supply connections, leaving enclosure 42 via openings provided with sealed passages, not represented in the drawing, the first resistor capable of serving as a grill, when it is brought to a temperature of approximately 500° or 600° C., as in the case of traditional air ovens, and the second resistor 84 being located beneath the floor of the cooking enclosure 42 against which it is pressed. The ends of this heating resistor 84 are electrically connected to the outlet points of the regulation means 48 of enclosure 42. A second temperature sensor, constituted of a thermocouple 86, is located against a lateral surface of the cooking enclosure 42 and is electrically connected to temperature control 48. This thermocouple controls the electrical power provided to resistor 84 according to the difference existing between the temperature displayed by control 87 and the temperature measured by thermocouple 86. The cooking enclosure 42 is thermo-insulated by adding a heat insulating pad 88, such as alumina silicate.

A small cylindrical crown 90 is welded on the gas outlet opening 54, a T-shaped fixture 92 being force fitted on such crown, the lateral joint opening of this T-shaped fixture 92 being blocked, in a sealed manner, by a stop 94 crossed by a thread 95 of thermocouple 50. The latter element is located substantially at the center of the T-shaped fixture 92, and has no contact with its walls. Thermocouple 50 is of the type whose temperature variation curve over time is traced in FIG. 2, respectively under a steam atmosphere and under an air atmosphere. This thermocouple 50 has two respective build-up times to reach a set point temperature $T_c$ of 100° C. when it is respectively placed in contact with steam at 320° C. and with air at the same temperature, namely, a first build-up time (under steam) $t_v$ equal to approximately 10 seconds, and a second build-up time (under air) $t_a$ equal to approximately 75 seconds. The gas flow exiting from the enclosure 42 thus encounters thermocouple 50 "head on", and this optimizes the response of the thermocouple. Because of the way that it is fixed inside T-shaped fixture 92, sensor 50 is subject to thermal losses. By varying the closeness of sensor 50 with the opening of T-shaped fixture 92 which is open to free air, one can adjust the amount of thermal loss in such a way that when T-shaped fixture 92 is crossed by air, sensor 50 cannot reach the set point temperature $T_c$, and when this air contains a proportion $P_c$ of steam, or critical proportion, sensor 50 does reach the set point temperature. When the temperature in T-shaped fixture 92 reaches the set point temperature $T_c$ of 100° C., the electrical contact 96 linked to thermocouple 50 is opened, and this results in the deactivation of heating resistor 20 of steam generator 44, as will be described in detail hereinafter. Tests conducted by the Applicant have shown that an opening threshold of electrical contact 96 of thermocouple 50, comprised between 95° C. and 108° C., minimized the quantity of steam leaving enclosure 42 during cooking, and at the same time ensured renewal of steam in the enclosure, and thereby a convection, thus enabling shorter cooking times to be obtained than those usually found in traditional ovens.

The distribution device 46 of steam entering cooking enclosure 42 is located at the outlet of opening 52. This distribution device is constituted of a first metallic tube 108 embedded, by one of its ends, on outlet tube 64 of overheater 58. Tube 108 opens, from its other end, into a second tube 110, perpendicular to it, and blocked at each of its ends. This tube 110 comprises, along its entire length and its lower portion, a series of holes 112. These holes 112, preferably located in a zig-zag and distributed uniformly along its entire surface, are graduated so that the steam produced is very slightly over-pressured in order to easily reach the food placed in cooking enclosure 42.

The steam generator 44 is constituted externally of a casing 113, made of a plastic material such as polypropylene, and its internal design is similar to the generator represented in FIG. 5, i.e., comprising an electrical resistor 20 of a cartridge type, having a power of approximately 1250 watts, and a porous body 22, compressed around such resistor 20, preferably constituted of quartz wool. At one end of resistor 20 a bimetal 115 is located, whose electrical contacts are closed in a resting position, the contacts being placed in an open position as soon as the temperature exceeds given threshold of 130° C. A free space 117 is left between the upper surface of porous body 22 and the ceiling of casing 113, so as to enable expansion of the steam produced. A circular opening 104, closed by a screwable stop 106, is provided on the upper surface of casing 113 so as to enable the steam generator 44 to be filled with water.

Figure 8:
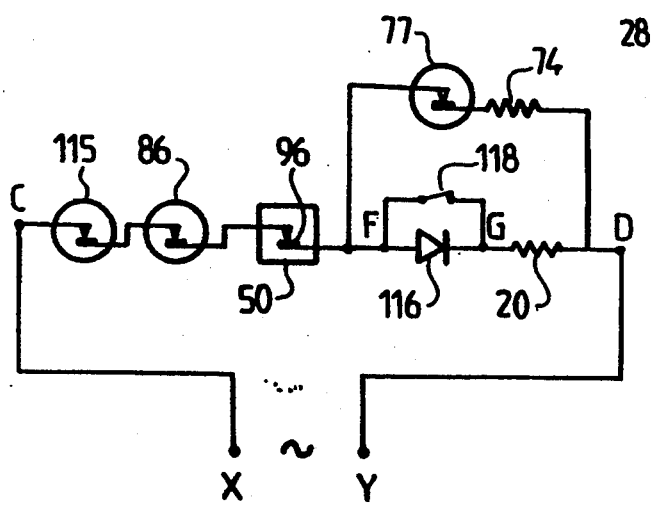
FIG. 8 is a diagrammatic view of an electrical supply circuit of the cooking oven of FIG. 7.

The electrical circuit with which the oven is provided according to the invention, and which is partially represented in FIG. 8, basically comprises two sub-assemblies. A first sub-assembly, that enables functioning of the temperature regulation means 48 and 76, and since these means do not have any special characteristics with respect to those equipping traditional ovens, will not be described here, and a second sub-assembly adapted to produce and heat steam and to adjust steam yield. This sub-assembly is constituted of a circuit powered by points X and Y of the electrical network. This circuit comprises, serially, between points C and D, safety and stoppage bimetal 115 in case of absence of water, thermocouple 86 for bringing enclosure 42 to the appropriate temperature, contact 96 of temperature sensor 50 for regulating steam yield according to the invention, a power diode 116 and heating resistor 20 of steam generator 44. A power reduction interrupter 118 is placed in parallel, at points F and G, to diode 116. When one wants to reduce the electrical power provided to resistor 20, interrupter 118 is opened and thereby reduces this power to approximately half of the nominal power, by rectifying one of two alternation of the alternating supply current. Resistor 74 of overheater 58, serially connected with an adjustment bimetal 77, is located in parallel between points F and D.

Given these conditions, the functioning of the oven according to the invention is as follows. Before activation the oven, the user fills porous body 22 of steam generator 44 with water, via opening 104, after removing stop 106, until such a time that the water level skims the upper surface of porous body 22. He selects a cooking mode by means of the temperature control 87 and steam temperature control 80 of the steam entering into enclosure 42, as well as the cooking duration. Naturally, the set point temperature can be acted upon by modifying thermal loss, for example by bringing sensor 5 closer to or further away from the free opening of tube 3.

As represented in FIG. 4, the Applicant has established, in substantially identical conditions, two pairs of curves of the same type (by using two different types of sensors), namely, a first pair of curves with an iron nickel sensor, respectively under air (curve $F_a$ and under steam ($F_v$), and a second pair of curves with a thermocouple also under a (curve $T_a$) and under steam (curve $T_v$), for an air and steam temperature of 135° C., close to a set point temperature $T_c$ of 85° C. As can be seen, curves $F_v$ and $T_v$ on the one hand, and $F_a$ and $T_a$ on the other hand are very close, which shows that steam detection according to the invention can be undertaken with sensors other than thermocouples, without substantial result variations.

The present invention is used, as represented in FIG. 5, to ensure the regulation of steam yield furnished by a steam generator.

The steam generator is constituted of a parallelopiped shaped enclosure 2, made of a plastic material such as, for example, polypropylene, and comprises, at its upper portion, an opening 4 blocked by a stop enabling enclosure 2 to be filled with liquid. Another opening 6 is also provided on the upper surface of enclosure 2, and is equipped with a flexible tube 8, for example made of silicon, that enables the steam produced by the generator to be evacuated. Tube 8 is interrupted, at a certain distance from enclosure 2, by a small T-shaped fixture 10, comprising a lateral opening 12. A stop 14 made of silicon is forced fitted in the lateral opening 12 of the T-shaped fixture 10 in order to ensure a perfect seal. This stop 14 is bored along its longitudinal axis with a very fine channel, through which a support wire 16 of temperature sensor 18 is introduced. This channel, compressed when stop 14 is pressed into T-shaped fixture 10, does not let the gases pass therethrough. The support wire 16 thus passes through stop 14 and temperature sensor 18 is located in such a way so as to be at the center of tube 8, without touching the walls of the latter.

The temperature sensor 18 used is a thermocouple of the type whose temperature variation curve over time under a steam and under an air atmosphere is represented in FIG. 2. This thermocouple 18 has two respective build-up times in order to reach a set point temperature $T_c$ of 100° C. when it is respectively in the presence of steam at 320° C. and air at the same temperature, namely a first build-up time (under steam) $t_v$ equal to approximately 10 seconds and a second build-up time (under air) $t_a$ equal to approximately 75 seconds.

Enclosure 2 comprises, additionally, an electrical resistor 20, for example of the cartridge type, that is, constituted of a tubular element made of stainless steel inside which the actual electrical resistor is housed, having a power of approximately 1200 watts, such tubular element being fixed, at its ends, to two lateral walls of enclosure 2, by fixing means not represented in the drawing.

A porous body 22, constituted for example of rock fibers, and preferably comprising a bond adapted to especially promote its mechanical retention, is located in a compressed state, in enclosure 2 around resistor 20 so as to ensure good mechanical contact therewith, and thereby, a good heat transfer. A space 21 is left free between the upper surface of porous body 22 and the upper internal surface of enclosure 2 so as to allow expansion of the steam produced.

The present device is supplied with electrical power by means of an electrical control circuit represented in FIG. 6. At points X and Y of the electrical network are successively connected, serially, a general interrupter 28, a contact 26 linked to temperature sensor 18, which enables current to pass through as long as the threshold temperature is not reached, a resistor 20 and a diode 30 being connected at points C and D from which an interrupter 32 is mounted in parallel, this interrupter 32 allowing, when it is open, only to let half the nominal power of the generator to pass through, such that, for example, the oscillation phases of sensor 18 are slowed down.

In these conditions, the functioning of the steam generator is as follows. Before activation, the user introduces the liquid to be steamed in enclosure 2 via opening 4, after removing the closure stop, until the level of the liquid skims the base of porous body 22. During the activation of the device, that is as soon as the general interrupter 28 is closed, resistor 20 of the steam generator starts to heat the liquid contained by impregnation in porous body 22. At the end of a given period of time, the water contained in porous body 22 surrounding resistor 20 reaches its boiling point, and starts to produce steam. The steam produced first pushes out the air initially present in enclosure 2, which leaves via tube 8.

The steam yield of the steam generator will be such that the total evacuation of air contained in space 21 of enclosure 2 is obtained in a time less than the under air build-up time $t_a$ of sensor 18, i.e., in the present case, less than 75 seconds, in order to stop sensor 18 from reaching the set point temperature $T_c$ before all the air from enclosure 2 has been evacuated, which could result in a premature stop of steam production.

This air evacuation phase continues as long as most of the air is not driven out by the steam, and as long as a substantial quantity of steam is not present in the evacuated air. Once the exiting air steam flow is basically constituted of steam, there is a quick rise in the temperature of sensor 18, and when this temperature exceeds the set point temperature $T_c$ of 100° C., after a time period necessarily greater than $t_v$, (i.e., in the present case, 10 seconds), contact 26 of thermocouple 18 opens, cutting thereby resistor 20 of the generator. The enclosure is then filled with steam. The steam production is interrupted and the generator passes to the resting state. As soon as the steam flow is suppressed in tube 8, the temperature of temperature sensor 18 starts to fall below set point temperature $T_c$ of 100° C., and contact 26 of the sensor is closed, retriggering steam production. A maintenance cycle can thus be established, comprising a periodic steam production ensuring a constant filling of steam in enclosure 2.

Indeed, as long as the composition of the gas leaving the cooking enclosure 42 is not sufficiently rich in steam, temperature sensor 50 does not reach the set point temperature $T_c$ (equal here to 100° C.) and the generator continues to produce steam and to furnish such steam to cooking enclosure 42. As soon as air is driven out from cooking enclosure 42, the gas exiting from it is then constituted of steam having a build-up time $t_v$ of 10 seconds and brings, at the end of this time-period, temperature sensor 50 to the set point temperature $T_c$, which results in contact 96 being opened and the electrical supply of heating resistor 20 of steam generator 44 being cut off.

It must be noted that the latter must have a steam yield that is high enough so that, between the moment when air starts to leave cooking enclosure 42 and the moment when the totality of air is driven from it, the elapsed time-period is less than build-up time $t_a$ of temperature sensor 50 in air (which, in the present case, is approximately 75 seconds), so as to stop temperature sensor 50 from reaching the set point temperature $T_c$ when there is still some air within cooking enclosure 42.

On the other hand, during cooking, and generally at the start of cooking, steam condenses on the food and the food consumes such steam, and this creates a situation for external air to enter. This air, at room temperature, thus comes into contact with sensor 50, such that its temperature drops, and this has the effect of starting steam generator 44 which then very quickly produces a quantity of steam that replaces the air entered inside cooking enclosure 42, and drives it, as well as any excess steam, out. Any passage of this steam on sensor 50 for at least a time $t_v$ (10 seconds here) will result in, as previously, the steam generator 44 being stopped.

Inversely, at the end of cooking, when the food is hot, it gets dehydrated, resulting in steam being released towards the outside, which is detected by sensor 50, which then triggers the deactivation of heating resistor 20 of steam generator 44.

The present invention thus enables steam consumption to be minimized, and this is advantageous on the one hand, in view of the water and electric consumption of the oven and, on the other hand, in view of comfort of use, because the amount of steam emitted in the cooking area is substantially reduced.

Additionally, the present invention enables one to ensure, in the cooking enclosure, convectional movements of the steam, such movements improving heat exchanges.

The process and device, according to the present invention can also be used for determining the quantity of steam contained in a gaseous air/steam mixture.

Figure 9:
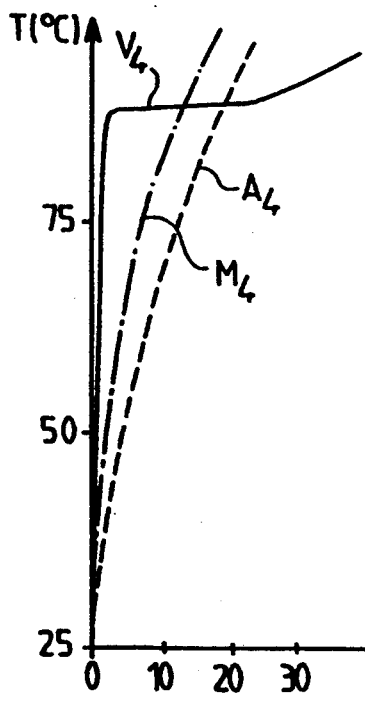
FIG. 9 is a graph representing the temperature reached by a heat sensor over the time during which it was respectively subject to an atmosphere of steam at a given temperature, and to an atmosphere of air at the same temperature, and to an atmosphere constituted of a mixture comprising 40% steam and 60% air at said same temperature.

Indeed, in FIG. 9, the temperature taken by a temperature sensor is represented, such sensor being constituted of a thermocouple, over the time-period during which it is respectively placed in contact with steam at 135° C. (curve $V_4$), with air at 135° C. (curve $A_4$) and with a mixture constituted of 40% steam and 60% air (curve $M_4$) at 135° C.

It must be noted that the time taken by the probe to reach a given set point temperature is intermediate between the one taken by the probe to reach the same temperature in environments constituted of only of steam and only of air. As such, this time is graduated in accordance with the proportion of steam in the air, and therefore one can measure this proportion by analyzing the time taken to reach the set point temperature.

We claim:

1. A steam cooking oven including a cooking enclosure supplied with steam from a steam generator, said cooking enclosure being in communication with ambient atmosphere through at least one outlet opening, and comprising:
   at least one temperature sensor, located along an outlet path of gas exiting from said outlet opening, said temperature sensor having two respective temperature build-up times, including one temperature build-up time under steam and one temperature build-up time under air, said sensor reaching a predetermined set point temperature when said sensor is in the presence of steam and in the presence of air; and
   controls means for controlling said steam generator, said control means being connected to said sensor to stop operation of said steam generator when said sensor reaches said set point temperature.

2. A steam cooking oven as defined by claim 1, further comprising means for subjecting the gas flow exiting from said enclosure to a thermal loss in a zone located in the vicinity of said temperature sensor, said thermal loss being such that when the gas flow is free of steam, said temperature sensor does not reach said set point temperature, and when the gas flow contains a predetermined proportion of steam, said temperature sensor reaches said set point temperature.

3. A steam cooking oven as defined by claim 1, wherein said temperature sensor is located downstream from said outlet opening of said cooking enclosure, in a zone subject to thermal losses.

4. A steam cooking oven as defined by claim 3, wherein said zone subject to thermal losses is located in a tube, one end of said tube being in communication with said outlet opening and another end of said tube being open to free air.

5. A steam generator including an enclosure in which water to be steamed is stored, steaming means for bringing the water contained in enclosure to a boil, and means for delivering, at an outlet of said enclosure, a gas flow of steam and/or air, and comprising:
   at least one temperature sensor located in an outlet path of the gas flow, said temperature sensor having two respective temperature build-up times, representing a temperature build-up time under steam and a temperature build-up time under air, such that said sensor can reach a predetermined set point temperature when said sensor is in the presence of steam and in the presence of air;
   means for subjecting the gas flow exiting from the steam generator to a thermal loss in a zone located in the vicinity of said temperature sensor, said thermal loss being such that when the gas flow is free of steam, said temperature sensor does not reach said set point temperature, and when the air flow contains a predetermined proportion of steam, said temperature sensor reaches said set point temperature; and
   control means for controlling said steaming means, said control means being connected to said temperature sensor in order to stop the operation of said steaming means when said temperature sensor reaches said set point temperature.

6. A steam generator as defined by claim 5, wherein said steaming means is capable of producing steam that is adequate to drive out the air contained within said enclosure in a time-period shorter than said under air temperature build-up time of said sensor.

7. A steam generator as defined by claim 5, wherein said zone subject to thermal losses is located in a tube, one end of said tube being in communication with said gas flow and another end of said tube being open to free air.

8. An apparatus for detecting the presence of steam in a volume of air at a predetermined temperature, comprising:
   at least one temperature sensor having two temperature build-up times, including a temperature build-up time under steam and a temperature build-up time under air, such that said sensor can reach a predetermined set point temperature lower than said predetermined temperature, when said sensor is in the presence of steam and in the presence of air;

means associated with said at least one temperature sensor for taking a temperature measurement with said sensor and providing an output signal; and means utilizing the output signal for determining if the temperature measured reaches said set point temperature in order to indicate whether said sensor is in the presence of steam.

9. The device according to claim 8, wherein said sensor is located in the vicinity of an outlet opening of an enclosure supplied with steam, in order to detect when said steam exits from said outlet opening.

10. The device according to claim 8, further comprising means for defining a zone, in the vicinity of said temperature sensor, that is subject to a thermal loss, such that said sensor does not reach said set point temperature when an air flow in said zone is free of steam, and said sensor reaches said set point temperature when the air flow contains a predetermined portion of steam.

11. The device according to claim 10, wherein said zone subject to a thermal loss is located inside a tube crossed by said volume of air, one end of said tube being supplied with said volume of air, the other end of said tube being open to free air.

12. The device according to claim 8, further comprising means for placing said temperature sensor in the presence of said volume of air for a time period shorter than said build-up time under air and at least equal to said build-up time under steam.

13. A device for determining the percentage of steam contained in a mixture of air and steam at a predetermined temperature, comprising:

at least one temperature sensor having two temperature build-up times, one temperature build-up time under steam and one temperature build-up time under air, capable of reaching a predetermined set point temperature, lower than said predetermined temperature, when said sensor is in the presence of steam and in the presence of air;

means for placing said sensor in the presence of said mixture until said sensor reaches said set point temperature;

means for measuring a temperature build-up time of said sensor in said mixture; and means for determining the difference between said measured temperature build-up time of said sensor with said temperature build-up times under steam and under air of said sensor, so as to determine the proportion of steam contained in said mixture.

14. A process for detecting the presence of steam in a volume of air at a predetermined temperature, comprising the steps of:

placing, in the presence of said volume of air, at least one temperature sensor having two respective temperature build-up times, one temperature build-up time under steam and one temperature build-up time under air, such that said sensor can reach a predetermined set point temperature, lower than said predetermined temperature, when said sensor is in the presence of steam and in the presence of air;

performing a temperature measurement with said sensor; and determining if the temperature measured reaches said set point temperature for indicating whether said sensor is in the presence of steam.

15. The process according to claim 14, further comprising the step of placing said temperature sensor in the presence of said volume of air in a zone subject to thermal losses, such that when said volume of air is free of steam, said temperature sensor does not reach said set point temperature, and when said volume of air contains a predetermined portion of steam, said temperature sensor reaches said set point temperature.

16. The process according to claim 14, further comprising the step of placing said temperature sensor in said volume of air during a time period shorter than said build-up time under air and at least equal to said build-up time under steam.

17. A method for determining the proportion of steam contained in a mixture of air and steam at a predetermined temperature, comprising the steps of:

determining, for at least one temperature sensor and in at least one range of predetermined set point temperatures, the temperature build-up times to reach a predetermined set point temperature under steam and under air;

placing said temperature sensor in the presence of said mixture until it reaches said set point temperature;

measuring a temperature build-up time of said sensor in said mixture; and determining the difference between said measured temperature build-up time measured of said sensor with said determined temperature build-up times under steam and under air of said sensor, in order to determine the proportion of steam contained in said mixture.

* * * * *